United States Patent
Bunel et al.

(10) Patent No.: US 6,372,939 B1
(45) Date of Patent: Apr. 16, 2002

(54) PRODUCTION OF 6-AMINOCAPROIC ACID

(75) Inventors: Emilio E. Bunel; Theodore A. Koch, both of Wilmington; Ronnie Ozer, Arden; Sourav K. Sengupta, Wilmington, all of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/713,143

(22) Filed: Nov. 16, 2000

(51) Int. Cl.[7] ............. C07C 205/00; C07C 207/00; C07C 229/00
(52) U.S. Cl. .............. 562/553; 562/531; 528/310; 528/323; 528/326
(58) Field of Search ............. 562/531, 553; 528/310, 323, 326

(56) References Cited

U.S. PATENT DOCUMENTS

| | | | |
|---|---|---|---|
| 1,628,190 A | | 5/1927 | Raney |
| 2,828,337 A | * | 3/1958 | Whitaker ............ 260/530 |
| 3,496,215 A | | 2/1970 | Drinkard |
| 4,470,928 A | * | 9/1984 | Kimura et al. .......... 260/239.3 |
| 4,730,040 A | | 3/1988 | Vagt et al. |
| 4,767,856 A | * | 8/1988 | Dockner et al. ......... 540/538 |
| 5,597,888 A | | 1/1997 | Nielinger et al. |
| 5,710,344 A | | 1/1998 | Breikss et al. |
| 5,821,378 A | | 10/1998 | Foo et al. |
| 5,840,959 A | | 11/1998 | Lane |
| 5,973,143 A | | 10/1999 | Guit et al. |
| 5,986,126 A | | 11/1999 | Bunel et al. |
| 6,005,145 A | | 12/1999 | Cordier et al. |
| 6,048,997 A | | 4/2000 | Fischer et al. |
| 6,069,246 A | | 5/2000 | Chiarelli et al. |

FOREIGN PATENT DOCUMENTS

WO        WO 98/04515 A1        2/1998

OTHER PUBLICATIONS

Reduction in Organic Chemistry. pp. 136–137. Milos Hudlicky. Halsted Press (1984).*

* cited by examiner

*Primary Examiner*—James O. Wilson
*Assistant Examiner*—Zachary Tucker
(74) *Attorney, Agent, or Firm*—Gerald E. Deitch

(57) ABSTRACT

A process for making 6-aminocaproic acid by hydroformylating 3-pentenenitrile to produce 3-, 4-, and 5-formylvaleronitrile (FVN mixture), oxidizing the FVN mixture to produce 3-, 4-, and 5-cyanovaleric acid; hydrogenating the resulting product to produce 6-aminocaproic acid, 5-amino-4-methylvaleric acid, and 4-amino-3-ethylbutyric acid; and isolating 6-aminocaproic acid from the reaction product. The resulting 6-aminocaproic acid can be cyclized to produce caprolactam.

20 Claims, No Drawings

PRODUCTION OF 6-AMINOCAPROIC ACID

FIELD OF THE INVENTION

The present invention concerns a process to produce 6-aminocaproic acid and optionally caprolactam.

BACKGROUND OF THE INVENTION

6-Aminocaproic acid is an intermediate in the production of caprolactam and/or nylon-6. Commercially, caprolactam is made by a process using cyclohexane as the starting material. Caprolactam is then polymerized to produce nylon-6. For cost reasons, it would be desirable to produce caprolactam from butadiene, a four carbon starting material, rather than the six carbon cyclohexane starting material currently used in commercial processes.

It is known that butadiene can be hydrocyanated to produce 3-pentenenitrile (3PN), which can be converted to caprolactam. One process for converting 3PN to caprolactam involves converting 3PN to adiponitrile (ADN). ADN is then partially hydrogenated to 6-aminocapronitrile, which is then converted to caprolactam by hydrolysis followed by cyclization. See for example, U.S. Pat. No. 6,069,246. The partial hydrogenation reaction produces a significant amount of hexamethylenediamine (HMD).

A second process for converting 3PN to caprolactam involves reductive amination of 5-formylvaleronitrile, which is derived by hydroformylation of 3-pentenenitrile. The reductively aminated product is then subjected to hydrolysis and cyclization. U.S. Pat. No. 6,048,997 discloses a process in which a mixture of 2-, 3-, and 4-pentenenitrile is reacted with carbon monoxide and hydrogen in the presence of a catalyst containing at least one Group VIII metal to produce a mixture comprising 3-, 4-, and 5-formylvaleronitrile. U.S. Pat. No. 5,986,126 teaches that 5-formylvaleronitrile is unstable and that the separation of 5-formylvaleronitrile from the branched 3- and 4-formylvaleronitriles is impractical because of yield losses that are suffered in distillation. To avoid this problem, U.S. Pat. No. 5,986,126 teaches that the separation of the linear product from the branched isomers is possible downstream after reductive amination of the formylvaleronitriles to produce aminonitriles (such as 6-aminocapronitrile) and diamines. In this second process, a significant amount of HMD is produced.

Both of the two 3PN-based processes described above produce significant amounts of HMD. It is not always desired to have HMD as a co-product in a commercial caprolactam operation. Thus, there is a need for a process that converts butadiene to caprolactam without the production of significant amounts of HMD. The present invention provides such a process.

BRIEF SUMMARY OF THE INVENTION

The present invention is a process for making 6-aminocaproic acid that comprises: (a) reacting 3-pentenenitrile with carbon monoxide and hydrogen in the presence of a hydroformylation catalyst comprising a Group VIII metal to produce a first reaction product which comprises 3-, 4-, and 5-formylvaleronitrile (FVN); (b) isolating from the first reaction product a FVN mixture consisting essentially of 3-, 4-, and 5-formylvaleronitrile; (c) contacting the FVN mixture with a molecular oxygen-containing gas for a time sufficient to oxidize the FVN mixture to produce a second reaction product which comprises 3-, 4-, and 5-cyanovaleric acid; and (d) reacting the second reaction product with hydrogen in the presence of a hydrogenation catalyst to produce a third reaction product which comprises 6-aminocaproic acid, 5-amino-4-methylvaleric acid, and 4-amino-3-ethylbutyric acid. 6-aminocaproic acid, either isolated from the third reaction product or reacted as part of the third reaction product, can be cyclized to produce a fourth reaction product comprising caprolactam. Alternately, the 6-aminocaproic acid can be converted directly to nylon-6.

DETAILED DESCRIPTION OF THE INVENTION

Production of 3-Pentenenitrile

3-Pentenenitrile (3PN) is produced commercially as an intermediate in the production of adiponitrile. The synthesis of 3PN is well known in the art. See for example, U.S. Pat. Nos. 3,496,215 and 5,821,378, the disclosures of which are incorporated herein by reference.

Hydroformylation of 3-Pentenenitrile

The hydroformylation of 3-pentenenitrile (i.e., the reaction of 3-pentenenitrile with carbon monoxide and hydrogen) to produce a reaction product which comprises 3-, 4-, and 5-formylvaleronitrile (FVN) can be carried out in the presence of a catalyst comprising a Group VIII element. The hydroformylation reaction temperature can vary from room temperature to about 200° C., preferably between 50 and 150° C. The pressure is preferably between 0.15 and 10 MPa and more preferably 0.2 to 5 MPa.

Preferred catalysts are rhodium compounds. Examples of suitable compounds include $Rh(CO)_2(DPM)$, [DPM=t—$C_4H_9$—COCHCO—t—$C_4H_9$]; $Rh(CO)_2(acac)$, [acac=acetylacetonate]; $Rh_2O_3$; $Rh_4$ (CO) 12; Rh6 (CO) 16; $[Rh(OAc)_2]_2$, [OAc=acetate]; and $Rh(ethylhexanoate)_2$. Preferably, the catalyst is $Rh(CO)_2(acac)$, $Rh(CO)_2(DPM)$, or $[Rh(OAc)_2]_2$.

These catalysts can be used in combination with phosphorous-containing ligands such as monodentate or bidentate phosphines, phosphonites, phosphinites, or phosphite compounds. Examples of such ligands include triarylphosphites, such as triphenylphosphite; triarylphosphines, such as triphenylphosphine; and bis (diarylphosphino)alkanes, such as diphenylphosphinoethane. In addition, polydentate phosphite compounds may be used as ligands. An example of these includes compounds having a structural formula as follows:

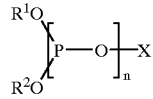

where $R^1$ and $R^2$ are the same or different mono-valent aryl groups, X is an n-valent organic bridging group, and n is an integer between 2 and 6. $R^1$ and $R^2$ may be substituted. Such ligands are described, for example, in U.S. Pat. No. 5,710,344, the disclosure of which is incorporated herein by reference.

The mole ratio of 3-pentenenitrile to catalyst is generally 100:1 to 100,000:1, preferably 500:1 to 10,000:1. The mole ratio of ligand to rhodium is typically between 0.5:1 and 10:1.

The mole ratio of hydrogen to carbon monoxide for hydroformylation reactions is typically in the range of 100:1 to 1:10, preferably in the range of 4.0:1 to 0.5:1. Inert gases may also be present in the hydrogen and carbon monoxide feed stocks.

The hydroformylation reaction may be performed in the presence of a solvent. Suitable solvents include inert solvents or a solvent consisting of the hydroformylation products themselves. Suitable inert solvents include aromatic hydrocarbons, hydrocarbons, nitriles, ethers, amides and urea derivatives, saturated hydrocarbons, and ketones. Some examples of suitable solvents include toluene, cyclohexane, benzene, xylene, Texanol® (2,2,4-trimethyl-1,3-pentanediol monoisobutyrate), diphenylether, tetrahydrofuran, cyclohexanone, benzonitrile, N-methylpyrrolidinone, and N,N-dimethylethylurea.

The hydroformylation reaction can be performed in a continuous or batch mode. The reaction can be performed in a variety of reactors, such as bubble column reactors, continuously stirred tank reactors, trickle bed reactors, and liquid-overflow reactors. Unreacted hydrogen, carbon monoxide, 3-pentenenitrile, and any solvent may be recovered and recycled to the hydroformylation reactor.

The hydroformylation reaction product comprises 3-, 4-, and 5-formylvaleronitriles, as well as unconverted 2-, 3-, and 4-pentenenitrile, catalyst, and high boilers. The separation of the FVN mixture from the catalyst and high boilers can be effected by utilizing thermally gentle evaporation techniques, known to those skilled in the art. Such techniques include the use of single stage flash evaporators, such as rolling-film evaporators, falling-film evaporators, or wiped-film evaporators. High boilers and catalyst separated from the FVN mixture can be recycled back to the hydroformylation reactor.

To avoid the decomposition of the catalyst and FVN mixture, a short contact time during flash evaporation is generally preferred. The contact time can vary between 1 second and 1 hour and preferably is between 1 and 5 minutes. The flash evaporation is carried out under commercially viable operating conditions. The temperature should be in the range of 75 to 200° C. The preferred range is 100 to 130° C. The pressure can vary from 13.3 to 1333 Pa, preferably 66.6 to 666.5 Pa.

Oxidation of Formylvaleronitriles

5-Cyanovaleric acid can be made by oxidation of 5-formylvaleronitrile by a process similar to that taught in U.S. Pat. No. 5,840,959, where methyl-5-formylvalerate is oxidized to produce monomethyladipate.

The FVN mixture is contacted with a molecular oxygen-containing gas for a time sufficient to oxidize the FVN mixture to produce a reaction product containing 3-, 4-, and 5-cyanovaleric acid. FVN can be oxidized with or without a catalyst and at atmospheric or elevated pressure. U.S. Pat. Nos. 4,537,987 and 4,931,590 teach that alkali metal oxides (such as potassium hydroxide or sodium hydroxide in amounts of 0.001 to 0.5% by weight) and metal salts of cobalt or manganese (such as cobalt acetate or manganese acetate in amounts of 0.0001 to 0.1% by weight) can be used to accelerate the oxidation reaction. While these catalysts can be used with the present invention, it is preferred to run the oxidation reaction in the absence of such catalysts.

Preferably, the oxidation is performed at elevated pressure in the presence of air. Such reaction conditions give a high conversion rate. The reaction may be run as a continuous process.

To obtain high conversion and selectivity, a pressure above atmospheric pressure (about 1 MPa) and preferably above 10 bars (1 MPa) of air is required. More preferably, the total pressure when using air should be about 20 bars (2 MPa) or higher. While higher pressures, e.g., 40 to 65 bars (4 to 6.5 MPa), may improve reactivity, they can necessitate higher equipment cost. Pressures of from about 20 to 40 bars (2 to 4 MPa) air represent a realistic and commercially acceptable range.

The oxidation step of the present invention can be performed at a temperature of from about 20° C. to as high as about 120° C. Preferably, the temperature is in the range of about 40° C. to about 80° C. Since the oxidation is exothermic, operating a commercial reactor at about 50° C., and above, is preferred as heat removal and associated cost become economic considerations. It is preferable to choose a temperature that allows the use of normal, low-cost cooling water.

The actual method of commercially implementing the oxidation process according to the present invention can be by any non-catalytic, heterophase, air oxidation method, as generally known in the art, including, by way of example, but not by limitation, batch reactor with or without stirring, continuous reactor with plug flow or back-mixing, counter-current reactor and the like. U.S. Pat. No. 5,840,959 teaches that for oxidation of alkyl 5-formylvalerate, realistic heat removal considerations cause the preferred method of reactor operation to be at less than optimum conversion. However, due to the high boiling point of the 3-, 4-, and 5-cyanovaleric acids in the present invention, it is preferred to run the oxidation reaction at the highest possible conversion and selectivity. Such an operation avoids the need to run a recycle loop with its associated distillation requirements.

Hydrogenation of Cyanovaleric Acids

Hydrogenation of the nitrile group to produce 6-aminocaproic acid from 5-cyanovaleric acid, can be accomplished in the presence of a metal catalyst, and optionally in a liquid solvent. Suitable metal catalysts can be of many types. The catalyst is used in an amount effective to catalyze the reaction. For example, sponge metal catalysts, homogeneous catalysts, and reduced metal oxide and mixed metal oxide catalysts may be used. Supported metal catalysts may also be used. Suitable active metals include iron, ruthenium, rhodium, iridium, palladium, cobalt, nickel, chromium, osmium, and platinum.

Sponge metals are one class of catalysts useful for the present invention. A sponge metal has an extended "skeleton" or "sponge-like" structure of metal, with dissolved aluminum, and optionally contains promoters. The sponge metals may also contain surface hydrous oxides, absorbed hydrous radicals, and hydrogen bubbles in pores. Sponge metal catalysts can be made by the process described in U.S. Pat. No. 1,628,190, the disclosure of which is incorporated herein by reference.

Preferred sponge metals include nickel, cobalt, iron, ruthenium, rhodium, iridium, palladium, and platinum. Sponge nickel or sponge cobalt are particularly suitable as catalysts. The sponge metal may be promoted by one or more promoters selected from the group consisting of Group IA (lithium, sodium, and potassium), IB (copper, silver, and gold), IVB (titanium and zirconium), VB (vanadium), VIB (chromium, molybdenum, and tungsten), VIIB (manganese, rhenium), and VIII (iron, cobalt, nickel, ruthenium, rhodium, palladium, osmium, iridium, and platinum) metals. The promoter can be used in an amount useful to give desired results. For example, the amount of promoter may be any amount less than 50% by weight of the sponge metal, preferably 0 to 10% by weight, more preferably 1 to 5% by weight.

Sponge nickel catalysts contain mainly nickel and aluminum. The aluminum is typically in the form of metallic aluminum, aluminum oxides, and/or aluminum hydroxides. Small amounts of other metals may also be present either in their elemental or chemically bonded form, such as iron and/or chromium, and may be added to the sponge nickel to increase activity and selectivity for the hydrogenation of certain groups of compounds. It is particularly preferred to use chromium and/or iron promoted sponge nickel as a catalyst.

Sponge cobalt catalysts also contain aluminum and may contain promoters. Preferred promoters are nickel and chromium, for example in amounts of about 2% by weight based on the weight of the catalyst.

Examples of suitable sponge metal catalysts include Degussa BLM 112W, W. R. Grace Raney® 2400, Activated Metals A-4000™, and W. R. Grace Raney® 2724.

Supported metal hydrogenation catalysts are another kind of useful catalysts for the present invention. Such catalysts consist of a metal catalyst on a solid support. Any such catalyst may be used in catalytically effective amounts. Preferred metals in the supported metal catalyst include ruthenium, nickel, cobalt, iron, rhodium, iridium, palladium, and platinum. Ruthenium is especially preferred. More than one metal may be used. Any solid support that does not interfere with the reaction can be used. Preferred solid supports include titanium dioxide, porous aluminum oxide, silicon dioxide, aluminum silicate, lanthanum oxide, zirconium dioxide, activated charcoal, aluminum silicate, silicon dioxide, lanthanum oxide, magnesium oxide, zinc oxide, and zeolites.

Particularly preferred solid supports are titanium dioxide, porous aluminum oxide, silicon dioxide, zirconium dioxide, and activated charcoal. Especially useful supported metal catalysts are supported ruthenium catalysts, for example, ruthenium on titanium dioxide. Also, it is acceptable to use a mixture of more than one support and/or more than one catalyst element.

Any method of placing the metal on the support may be used. Several methods are known in the art. One method uses vapor deposition of the metal onto the support. Another method uses a flame spray technique to apply the metal to the support. Another method applies a solution of the metal salt or metal oxide to the support. This step is followed by drying of the support and then reducing the salt or oxide. Another method applies a metal salt that can easily be thermally decomposed to the support. Suitable metal salts include carbonyl or hydride complexes of one or more of iron, nickel, cobalt, ruthenium, rhodium, palladium, osmium, iridium, platinum, chromium, molybdenum, tungsten, manganese, rhenium, copper, silver, and gold.

The metal is typically applied to the solid support at 0.1 to 90 percent by weight relative to the total weight of the supported catalyst. Preferably, the metal is at 0.5 to 50% by weight, more preferably 2 to 25% by weight.

Homogeneous catalysts are another useful type of metal catalyst for the present invention. Homogeneous catalysts are soluble metal compounds incorporating one or a combination of a metal such as rhodium, ruthenium, cobalt, nickel, iron, palladium, or platinum, and a hydrocarbon-containing ligand which may also contain bonded to the metal atom an atom such as phosphorus, nitrogen, oxygen, carbon, and sulfur.

Another type of useful hydrogenation catalyst is derived from the reduction of at least one metal oxide, a mixture of metal oxides, or a mixture of metal oxide, hydroxide and/or carbonate. Such catalysts have similar structures to sponge metal catalysts in their extended "skeleton" metallic structure. However, they typically would not contain dissolved aluminum or silicon. Such catalysts can be prepared by the reduction of bulk metal oxides such as iron oxide or cobalt oxide. Alternately, the bulk metal oxide precursor may be prepared as a mixture of metal oxides including one or more of the oxides of iron, cobalt, nickel, ruthenium, rhodium, palladium, osmium, iridium, platinum, chromium, molybdenum, tungsten, and manganese. In addition, metal hydroxides or metal carbonates may be included in the metal oxide mixture. See WO 98/04515 and U.S. Pat. No. 6,005,145, the latter being incorporated herein by reference.

The hydrogenation reaction is normally performed at a pressure of 100 to 5000 psi (0.69 to 34.5 MPa), preferably 300 to 1500 psi (2.1 to 10.3 MPa), and more preferably 500 to 1000 psi (3.4 to 6.9 MPa). The hydrogen pressure is typically 50 to 4000 psi (0.34 to 27.6 MPa), preferably 100 to 1000 psi (0.69 to 6.9 MPa), and more preferably 250 to 750 psi (1.7 to 5.2 MPa). The molar ratio of hydrogen to 5-cyanovaleric acid is typically 2:1 to 200:1, more preferably, 2:1 to 100:1.

The hydrogenation reaction temperature is 40 to 220° C., preferably 70 to 150° C., more preferably 80 to 120° C.

The reaction is preferably carried out in the absence of air.

The hydrogenation reaction may optionally be performed in the presence of a solvent. Any solvent that does not interfere with the reaction may be used and can be used in an amount to increase the yield of the reaction and/or to remove heat from the reaction. Suitable solvents include water, alcohols, esters, hydrocarbons, tetrahydrofuran (THF), dioxane, ammonia, and ammonium hydroxide. Preferred solvents are ammonia, methanol, water, and mixtures of these solvents. Typically when a solvent is used, the mole ratio of solvent to 5-cyanovaleric acid is 1:1 to 100:1, preferably 5:1 to 40:1, more preferably 10:1 to 20:1.

Hydrogenation reactions may be performed in any suitable type of reactor. Suitable reactors include a fixed bed reactor and slurry reactor. A fixed bed reactor has an advantage of easy separation of the reactants and products from the catalyst. Slurry reactors include batch, a continuously stirred tank reactor, and a bubble column reactor. In slurry reactors, the catalyst may be removed from the reaction mixture by filtration or centrifugal action.

The amount of hydrogenation catalyst used will depend on the type of reactor used. For slurry reactors, the catalyst will make up 0.1 to about 30% by weight of the reactor contents. Preferably, the amount of catalyst will be 1 to 15% by weight, more preferably 5 to 10% by weight.

For a fixed bed reactor, the weight hourly space velocity will typically fall in the range of 0.05 to 100 $hr^{-1}$, preferably 0.1 to 10 $hr^{-1}$, more preferably 1.0 to 5.0 $hr^{-1}$.

In the present invention, the 5-cyanovaleric acid reactant may also contain 3- and 4-cyanovaleric acid, and, in such a situation, the product of the hydrogenation will contain 5-amino-4-methylvaleric acid, and 4-amino-3-ethylbutyric acid, in addition to the desired 6-aminocaproic acid and caprolactam products.

Isolation of 6-Aminocaproic Acid

Separation of 6-aminocaproic acid from its branched isomers can be easily accomplished by precipitation of the crude reaction mixture and/or crystallization in a solvent. Such techniques are well known by those skilled in the art. Isolated 6-aminocaproic acid can be purified by recrystallization. Recrystallization is a commonly used procedure for the purification of a compound, and consists of dissolving the crude (i.e., impure) compound in the minimum amount of solvent at an elevated temperature. Slow cooling of the resulting solution allows the preferential crystallization of the desired compound while leaving most of the impurities in solution. For 6-aminocaproic acid, the impurities that need to be removed are the branched isomers. Because of the high solubilities of 6-aminocaproic acid and its branched isomers in water or ammonium hydroxide, the presence of a different solvent and/or combination of solvents is generally required. The most appropriate solvents are those which present good miscibility with water and/or ammonium hydroxide. Examples of such solvents are alcohols, nitrites, ethers, ketones, carboxylic acids, esters, amides, sulfoxides and carbonates. Preferred solvents are methanol, ethanol, acetonitrile, tetrahydrofuran, dimethylsulfoxide, and dimethylformamide. The amount of 6-aminocaproic acid and branched isomers to be used in recrystallization is determined by the solubility of the compound at the desired recrystallization temperature.

Cyclization of 6-Aminocaproic Acid to Produce ε-Caprolactam

6-Aminocaproic acid can by cyclized to ε-caprolactam at elevated temperatures. U.S. Pat. No. 4,730,040, which is incorporated herein by reference, describes a process where 6-aminocaproic acid, formed by hydrolysis of methyl 5-formylvalerate, is heated to a temperature between 150 and 370° C. to produce ε-caprolactam. U.S. Pat. No. 5,973,143 discloses a process where 6-aminocaproic acid is converted to caprolactam by cyclizing the 6-aminocaproic acid in the presence of a solid acid/metal oxide catalyst and is incorporated herein by reference.

Polymerization of 6-Aminocaproic Acid to Produce Nylon-6 Polymer

Nylon-6 polymer can be produced by heating 6-aminocaproic acid. For example, Ullmann's Encyclopedia of Industrial Chemistry (Vol. A10 (1987), p572) reports that exposing 6-aminocaproic acid to a temperature of 250° C. produces an equilibrium mixture containing about 89% linear polyamide, 8.5% caprolactam, and 2.5% larger ring amides. This polymer was determined to be equivalent to polymer produced by condensation of ε-caprolactam. U.S. Pat. No. 5,597,888, incorporated herein by reference, discloses a process where 6-aminocaproic acid is heated at 160 to 200° C. for a time of 5 to 70 hours to produce nylon-6.

EXAMPLES

The present invention is exemplified by the following non-limiting examples.

Example 1
Air Oxidation of Formylvaleronitriles to Cyanovaleric Acids

This example shows that formylvaleronitriles can be oxidized to cyanovaleric acids.

5 grams of a mixture of formylvaleronitriles containing 96.9% of 5-formyl valeronitrile was heated at 80° C. under 1000 psi (6.9 MPa) of air for 1 hour. Orthodichlorobenzene was added as the internal standard and the mixture analyzed by gas chromatography with a Restex®-5 Amine column (15 m×0.25 mm). The composition of the reaction mixture (mole %) after the oxidation was: 2.5% 5-formylvaleronitrile (5FVN), 0.1 % 4-formylvaleronitrile (4FVN), 0.3% 3-formylvaleronitrile (3FVN), 94.1% 5-cyanovaleric acid (5CVA), and 1.3% 3-cyanovaleric acid (3CVA).

Example 2
Synthesis of 6-Aminocaproic Acid Using 5% Ru/TiO₂ Catalyst and Ammonium Hydroxide This example shows that 5-cyanovaleric acid can be hydrogenated to 6-aminocaproic acid in the presence of 5% by weight ruthenium on titanium dioxide support.

A 100 cc stainless steel (Parr reactor) stirred batch autoclave was used for the hydrogenation of 5-cyanovaleric acid (5CVA) in the presence of 5% Ru/TiO₂ catalyst. 10.0 g of 5CVA mixture (92.8% 5CVA, 3.1 % 3CVA, and 3.4% 4-cyanovaleric acid (4CVA)), 1.0 g of 1-methyl-2-pyrrolidinone (NMP, internal standard), 40.0 g of ammonium hydroxide solution, and 1.0 g of 5% Ru/TiO₂ were added in the reactor cup. The reactor was then assembled by securing the cup to the head, pressure tested with 100 psig (0.69 MPa) of nitrogen, and purged with nitrogen, followed by hydrogen. The reactor was then pressurized to 250 psig (1.8 MPa) with hydrogen and heated up to the reaction temperature (110° C.), under constant stirring. The pressure in the reactor was then brought up to the desired level (900 psig (6.3 MPa)) and maintained at that level throughout the entire duration of the run (4 hr). During the course of the reaction, samples (0.2 cc) were withdrawn periodically from the reactor through a sample port, connected to a dip leg inside the reactor, and analyzed by Hewlett-Packard 6890 gas chromatograph after derivatizing the sample with a mixture of bis-trimethylsilyl trifluoro acetamide (BSTFA) and trimethylchlorosilane. The conversion of 5CVA and selectivities and yields of 6-aminocaproic acid (6ACA) and caprolactam (CL) as a function of reaction time have been presented in Table 1.

TABLE 1

| Time (h) | Conversion of 5CVA | Selectivity of 6ACA (mole %) | Yield of 6ACA (mole %) | Selectivity of CL (mole %) | Yield of CL (mole %) |
|---|---|---|---|---|---|
| 0 | 0.0 | 0 | 0 | 0.0 | 0.0 |
| 1 | 34.2 | 78.3 | 26.7 | 0.0 | 0.0 |
| 2 | 99.8 | 85.8 | 85.6 | 0.2 | 0.2 |
| 3 | 100.0 | 86.3 | 86.3 | 0.3 | 0.3 |
| 4 | 100.0 | 86.4 | 86.4 | 0.4 | 0.4 |

Example 3
Synthesis of 6-Aminocaproic Acid Using 5% Ru/TiO₂ Catalyst and Ammonia This example shows that 5-cyanovaleric acid can be hydrogenated to 6-aminocaproic acid in the presence of 5% Ru/TiO₂ using liquid ammonia as solvent.

A 300 cc stainless steel (Autoclave Engineers) stirred batch autoclave was used for the hydrogenation of 5-cyanovaleric acid (5CVA) in the presence of 5% Ru/TiO₂ catalyst. 40.0 g of 5CVA mixture and 4.0 g of 5% Ru/TiO₂ were added in the reactor cup. The reactor was then assembled by securing the cup to the head, pressure tested with 100 psig (0.69 MPa) of nitrogen, and purged with hydrogen. After purging the reactor with hydrogen, 80 g of ammonia was added to the reactor. It was then pressurized to 300 psig (2.2 MPa) with hydrogen and heated up to the reaction temperature (110° C.), under constant stirring. The pressure in the reactor was then brought up to the desired level (1300 psig (9.1 MPa)) by adding hydrogen and maintained at that level throughout the entire duration of the run (5 hr). After 5 hours, the reactor was cooled down to 50° C. and the pressure was slowly released down to 100 psig (0.69 MPa). The product was then separated from the catalyst by forcing the same through a 5 microns filter connected to a dip leg inside the reactor. A small amount of the product was analyzed by Hewlett-Packard 6890 gas chromatograph after derivatizing the sample with a mixture of bis-trimethylsilyl trifluoro acetamide (BSTFA) and trimethylchloro silane. Approximately, 80% and 11.4% yields of 6ACA and CL, respectively, were achieved at 100% conversion of 5CVA.

Example 4
Separation of Linear and Branched Aminocaproic Acids

This example shows that 6-aminocaproic acid (ACA) can be separated from the hydrogenation product mixture by crystallization.

A 100 mL Parr autoclave was charged with 32.03 g of cyanovaleric acids (2.12% 3-cyanovaleric acid, 1.44% 4-cyanovaleric acid and 96.44% 5-cyanovaleric acid), 36 mL of NH$_4$OH, 2.51 g of 1-methyl-2-pyrrolidinone (GC internal standard) and 1.6 g of 5%Ru/TiO$_2$. The autoclave was evacuated and pressurized with hydrogen. After adding 16.2 mL of liquid ammonia with a syringe pump the reactor was brought to 1100C and a total pressure of 950 psig (6.7 MPa) with hydrogen. Samples were removed periodically from the autoclave and analyzed by gas chromatography after derivatizing the sample with a mixture of bis-trimethylsilyl trifluoro acetamide (BSTFA) and trimethylchlorosilane. The results are shown in Table 2. The content from the autoclave was removed and crystals were formed upon standing at room temperature. The solid was filtered, rinsed with ethanol and dried under vacuum. A small sample was dissolved in water, and reacted with BSTFA and then analyzed by gas chromatography. The sample contained: 1.61% 5ACA, 97.25% 6ACA and 1.14% iminobishexanoic acid (IBHA). The solid was recrystallized from a mixture of acetonitrile and water. Derivatization with BSTFA followed by gas chromatography indicated that the purity of 6-aminocaproic acid was 99.8 %.

TABLE 2

| Time (min) | 3CVA (wt %) | 4CVA (wt %) | 5CVA (wt %) | 4ACA (wt %) | 5ACA (wt %) | 6ACA (wt %) | IBHA (wt%) | 6ACA Yield |
|---|---|---|---|---|---|---|---|---|
| 0 | 2.10 | 1.48 | 96.42 | 0.00 | 0.00 | 0.00 | 0.00 | 0.00 |
| 15 | 1.89 | 1.30 | 84.04 | 0.53 | 0.00 | 12.05 | 0.20 | 12.22 |
| 30 | 1.74 | 1.15 | 74.28 | 0.60 | 0.00 | 21.80 | 0.45 | 22.03 |
| 60 | 1.46 | 0.89 | 58.40 | 0.00 | 0.00 | 40.04 | 1.22 | 40.50 |
| 90 | 1.21 | 0.67 | 41.19 | 0.00 | 0.00 | 54.92 | 2.00 | 56.44 |
| 125 | 0.99 | 0.48 | 28.34 | 0.58 | 0.08 | 66.67 | 2.86 | 67.11 |
| 182 | 0.65 | 0.23 | 11.99 | 0.00 | 0.08 | 83.26 | 3.79 | 85.32 |
| 240 | 0.36 | 0 | 3.57 | 0.00 | 0.09 | 91.78 | 4.19 | 90.93 |

What is claimed:

1. A process for making 6-aminocaproic acid comprising:
   (a) reacting 3-pentenenitrile with carbon monoxide and hydrogen in the presence of a hydroformylation catalyst comprising a Group VIII element to produce a first reaction product which comprises 3-, 4-, and 5-formylvaleronitrile (FVN);
   (b) isolating from the first reaction product an FVN mixture that consists essentially of 3-, 4-, and 5-formylvaleronitrile;
   (c) contacting the FVN mixture with a molecular oxygen-containing gas for a time sufficient to oxidize the FVN mixture to produce a second reaction product which comprises 3-, 4-, and 5-cyanovaleric acid; and
   (d) reacting the second reaction product with hydrogen in the presence of a hydrogenation catalyst to produce a third reaction product that comprises 6-aminocaproic acid, 5-amino-4-methylvaleric acid, and 4-amino-3-ethylbutyric acid.

2. The process of claim 1 further comprising isolating 6-aminocaproic acid from the third reaction product.

3. The process of claim 2 in which the hydroformylation catalyst is a rhodium compound.

4. The process of claim 3 in which the hydroformylation catalyst further comprises a ligand selected from the group consisting of phosphines, phosphonites, phosphinites, phosphites, and polydentate phosphites.

5. The process of claim 4 in which step (a) is performed at 50 to 150° C., a pressure of 0.15 to 10 MPa, a mole ratio of hydrogen to carbon monoxide of 100:1 to 1:10, and a mole ratio of 3-pentenenitrile to catalyst of 500:1 to 10,000:1.

6. The process of claim 5 wherein a single stage flash evaporator is used to isolate the first reaction product.

7. The process of claim 2 in which the molecular oxygen-containing gas is air.

8. The process of claim 7 in which step (c) is conducted at a temperature from 20 to 120° C. and at a pressure in excess of atmospheric pressure.

9. The process of claim 8 in which step (c) is carried out at a temperature from 40 to 80° C. and a pressure is in excess of 1 MPa.

10. The process of claim 9 in which the step (c) is carried out at a temperature from 40 to 80° C. and at a pressure of 2 to 4 MPa.

11. The process of claim 2 in which the hydrogenation catalyst comprises at least one element selected from the group consisting of iron, ruthenium, rhodium, iridium, palladium, cobalt, nickel, chromium, osmium, and platinum.

12. The process of claim 11 in which the hydrogenation catalyst is selected from the group consisting of sponge cobalt, sponge nickel, and ruthenium metal on a solid support.

13. The process of claim 12 wherein the sponge cobalt or sponge nickel catalyst contains at least one promoter selected from the group consisting of lithium, sodium, potassium, copper, silver, gold, titanium zirconium, vanadium, chromium, molybdenum, tungsten, manganese, rhenium, iron, cobalt, nickel, ruthenium, rhodium, palladium, osmium, iridium, and platinum, wherein the promoter is present in an amount equal to or less than 10% by weight of the sponge catalyst.

14. The process of claim 13 wherein the step (d) is performed at a hydrogen pressure of 1.7 to 5.2 MPa, a molar ratio of hydrogen to 5-cyanovaleric acid of 2:1 to 100:1, and in the presence of a solvent comprising ammonia, methanol, water, or mixtures thereof.

15. The process of claim 14 in which the hydrogenation catalyst is ruthenium metal on a solid support selected from the group consisting of titanium dioxide, aluminum oxide, zirconium dioxide, and activated charcoal.

16. The process of claim 15 wherein the solid support is titanium dioxide.

17. The process of claim 2 in which 6-aminocaproic acid is separated from the third reaction product by crystallization.

18. The process of claim 17 in which the separated 6-aminocaproic acid is purified by recrystallization from a solvent selected from the group consisting of methanol, ethanol, acetonitrile, tetrahydrofuran, dimethylsulfoxide, and dimethylformamide.

19. A process as in claim 1 or 2, further comprising: cyclizing 6-aminocaproic acid to form a fourth reaction product comprising caprolactam, and isolating caprolactam from the fourth reaction product.

20. A process as in claim 1 or 2, further comprising heating 6-amincaproic acid to form nylon-6 polymer.

* * * * *